United States Patent

Friese et al.

[11] Patent Number: 5,368,713
[45] Date of Patent: Nov. 29, 1994

[54] LAMINATED SYSTEM FOR GAS SENSORS AND PROCESS FOR PRODUCING IT

[75] Inventors: Karl-Hermann Friese, Leonberg; Hans-Martin Wiedenmann, Stuttgart; Eberhard Goehring, Schwieberdingen, all of Germany

[73] Assignee: Robert Bosch GmbH, Stuttgart, Germany

[21] Appl. No.: 39,059

[22] PCT Filed: Sep. 21, 1991

[86] PCT No.: PCT/DE91/00749
 § 371 Date: Apr. 5, 1993
 § 102(e) Date: Apr. 5, 1993

[87] PCT Pub. No.: WO92/07253
 PCT Pub. Date: Apr. 30, 1992

[30] Foreign Application Priority Data

Oct. 20, 1990 [DE] Germany .............. 4033388

[51] Int. Cl.$^5$ .................................. G01N 27/26
[52] U.S. Cl. ...................... 204/429; 204/424; 204/426
[58] Field of Search ............ 204/424, 426, 429; 427/453, 454, 126.1, 126.2, 383.5, 419.1, 419.2

[56] References Cited

U.S. PATENT DOCUMENTS

| | | | |
|---|---|---|---|
| 4,021,326 | 5/1977 | Pollner et al. | 204/195 S |
| 4,272,349 | 6/1981 | Furutani et al. | 204/424 |
| 4,296,148 | 10/1981 | Friese | 427/126.2 |
| 4,296,148 | 10/1981 | Friese | 427/126.2 |
| 4,863,583 | 5/1989 | Kurachi et al. | 204/429 |
| 5,089,299 | 2/1992 | Van'T Veen et al. | 427/419.2 |

FOREIGN PATENT DOCUMENTS

| | | |
|---|---|---|
| 0331513A2 | 9/1989 | European Pat. Off. . |
| 0369238A3 | 5/1990 | European Pat. Off. . |
| 0369238A2 | 5/1990 | European Pat. Off. . |
| 0373745A3 | 6/1990 | European Pat. Off. . |
| 2656648A1 | 6/1977 | Germany . |
| 62-14055 | 1/1987 | Japan . |

Primary Examiner—John Niebling
Assistant Examiner—Bruce F. Bell
Attorney, Agent, or Firm—Spencer, Frank & Schneider

[57] ABSTRACT

A layer system (11, 12) and a process for producing such a layer system is proposed which serves, in particular, to produce exhaust gas sensors. The modified layer system according to the invention advantageously contains very finely dispersed and highly reactive mixed oxides of alkali metals and at least trivalent elements on or in the porous covering layer (12), which mixed oxides exhibit an improved gettering action with respect to all the contaminants from the exhaust gas. Exhaust gas sensors having a layer system according to the invention are largely insensitive to contaminants from the exhaust gas.

14 Claims, 1 Drawing Sheet

LAMINATED SYSTEM FOR GAS SENSORS AND PROCESS FOR PRODUCING IT

BACKGROUND OF THE INVENTION

The invention relates to a layer system and a process for producing layer systems for gas sensors in accordance with the generic class of the main claim. Such layer systems are disclosed, for example, in German Patent Specification 28 52 647.

It has been found, however, that a porous covering layer on its own cannot always adequately protect the electrode layer against contaminants from the exhaust gas such as, for example, silicon, phosphorus, zinc, lead and their compounds. EP-A2-0 331 513 therefore proposed to introduce alkaline earth metal oxides onto the surface or into the pores of the covering layer. The gaseous organic or inorganic silicon compounds are thereby trapped and converted into stable compounds which do not impair the operation of the sensor. Although alkaline earth metal oxides are able to trap the contaminant silicon effectively to form refractory reaction products, they are able to trap lead only in the presence of other coreactants such as, for example, silicon and then only to form low-melting reaction products which result in a blocking of the pores in the protective layer and, consequently, in an impairment of the sensor sensitivity.

During the initial motor run after production of a motor vehicle, the contaminant silicon may occur, in particular as a result of escape from sealing parts, whereas, during continuous operation, pollutants such as, for example, lead, phosphorus, zinc, and in exceptional cases also silicon, primarily originating from fuel and oil additives may occur.

EP-A2-0 373 745 furthermore discloses protecting the electrode layer of fuel cells or gas sensors from silicon-containing and/or aluminium-containing compounds in the test gas by depositing one or more oxides, or compounds which form oxides on heating, of the metals from the group comprising Ce, Sm, Mg, Be, Ca, Sr, Ti, Zr, Hf, Y, La, Ce, Pr, Nb, Pm, Sm, Eu, Gd, Tb, Dy, Ho, Er, Tm, Yb, Lu, Th, U.

U.S. Pat. No. 4,272,349 discloses the use of an outer protective layer composed of $Al_2O_3$ which acts as a getter for catalyst poisons, in particular for phosphorus.

SUMMARY OF THE INVENTION

The claimed layer system having the features of the main claim has the advantage that the mixed oxides are able to trap the various contaminants usually occurring in exhaust gas such as, for example, silicon, phosphorus, zinc or lead. The combination of alkali metals, on the one hand, and at least trivalent elements, on the other hand, results in mixed oxides whose reactivity and thermal stability can be matched to the pollutants. The mixed oxide getters according to the invention react with the contaminants from the exhaust gas to form reaction products having high melting points above the maximum application temperature of the layer system. The high affinity of the alkali oxides for acidic oxides results in a beneficial gettering action with respect to silicon and phosphorus. The amphoteric or weakly acidic nature of the at least trivalent mixed oxide partner also results, in particular, in the gettering action for divalent contaminants such as, for example, lead or zinc.

Compared with the known contaminant getters, the invention consequently makes it possible to cover a wide contaminant spectrum.

As a result of the measures listed in the subclaims and in the process claims, advantageous further developments and improvements of the layer system specified in the main claim are possible. It is particularly advantageous to deposit the mixed oxides by impregnation from a preferably aqueous solution, for example of the nitrates or chlorides, or from solutions of organometallic compounds. The compounds of the alkali metals and of the trivalent or higher-valency elements are chosen in such a way that they decompose at temperatures just above the application temperature of the sensor, the mixed oxides being produced in very finely dispersed, highly reactive form. The impregnation process offers the further advantage that, in addition to the mixed oxides, catalyst substances, in particular noble-metal catalysts such as platinum, palladium, rhodium or others, can simultaneously be introduced into the porous covering layer in order to adjust the control point of the sensor.

According to a further advantageous embodiment, the mixed oxides are deposited as additional layers on the completely sintered layer system comprising solid electrolyte, electrode layer and porous covering layer or on the still unsintered layer system, which is then sintered together with this additional layer. In this case, the additional mixed-oxide-containing layer can be deposited directly on the electrode layer, on the porous covering layer or as an intermediate layer between the porous covering layer and a further porous covering layer.

Lithium aluminium oxide $Li_2O \cdot Al_2O_3$ has proved particularly advantageous. Further, particularly preferred lithium-containing mixed oxides are:

(2) $Li_2O \cdot Ga_2O_3$
(3) $2Li_2O \cdot Al_2O_3 \cdot Ga_2O_3$
(4) $0.02Li_2O \cdot 0.98Al_2O_3$
(5) $0.98Li_2O \cdot 0.02Al_2O_3$
(6) $Li_2O \cdot 0.9Al_2O_3 \cdot 0.1B_2O_3$
(7) $Li_2O \cdot Ln_2O_3$ (Ln = La, Nd, Sm, En, Gd, Dy, Er, Yb)
(8) $Li_2O \cdot Y_2O_3$
(9) $Li_2O \cdot ZrO_2$ ($ZrO_2$ with 1.5–2 wt. % $HfO_2$)
(10) $3Li_2O \cdot 2ZrO_2$ ($ZrO_2$ with 1.5–2 wt. % $HfO_2$)
(11) $Li_2O \cdot Na_2O \cdot 22Al_2O_3$
(12) $Li_2O \cdot Sc_2O_3$
(13) $0.1Li_2O \cdot 0.1Y_2O_3 \cdot 0.8ZrO_2$.

A further preferred mixed oxide is sodium β-aluminium oxide, $Na_2O \cdot 11Al_2O_3$.

Layer systems for exhaust gas sensors which determine the oxygen content, i.e. for lambda probes, can advantageously be produced by the process according to the invention. However, layer systems for other exhaust gas sensors, for example for CO, $(NO)_x$ or $(CH)_n$ sensors can also be produced by the process. The exhaust gas sensors produced in this way are largely insensitive to contaminants from the exhaust gas.

DESCRIPTION OF THE PREFERRED EMBODIMENT

Figure 1:
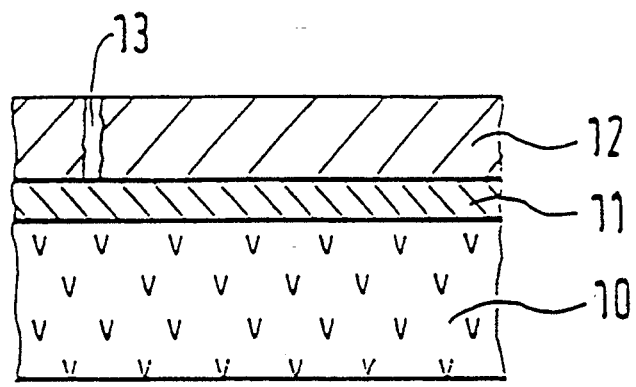
FIG. 1 is a highly schematic fragmentary cross-sectional view of a preferred embodiment of the layer system.
Figure 2:
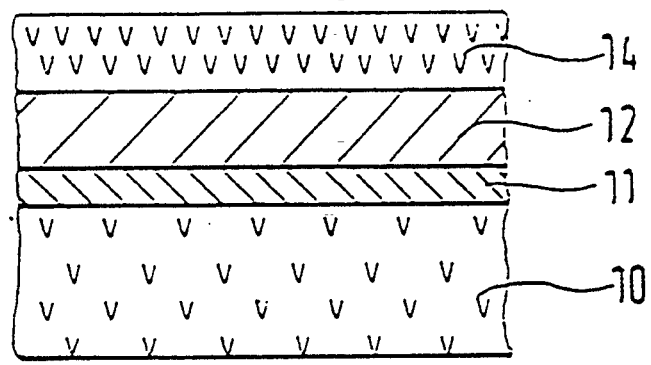
FIG. 2 is a highly schematic fragmentary cross-sectional view of yet another preferred embodiment of the layer system.

The starting point is a layer system in accordance with German Patent Specification 28 52 647. FIG. 1 shows a layer system comprising a standard solid electrolyte ceramic 10 composed of zirconium dioxide fully or partially stabilised with yttrium, a Cermet electrode 11 deposited thereon and composed of 60% by volume of platinum and 40% by volume of $Y_2O_3$-stabilised $ZrO_2$ powder, and a porous covering layer 12 composed of 75% by weight of $ZrO_2$/25% by weight of $Al_2O_3$. 13 denotes in simplified form one of the pores which are present in a large number in the sintered layer 12 and whose diameter is in the range from 0.2 to 15$\mu$m. The layer system is sintered in accordance with the data in German Patent Specification 28 52 647. FIG. 2 shows a layer system similar to that in FIG. 1 with an additional covering layer 14 comprising a mixed oxide as described in claim 1.

The sintered layer system 10, 11, 12 described above is immersed for 3 minutes in an equimolar solution of $LiNO_3$ and $Al(NO_3)_3$ at room temperature. Then the solution is allowed to drip off for about 10 minutes. The porous covering layer 12 can be virtually completely impregnated during the process cycle as a result of capillary forces. In a subsequent process step, the layer system 10, 11, 12 is heat-treated in air for two hours at 1000° C. so that the lithium aluminium mixed oxide can form from the nitrates in and on the porous covering layer 12.

The layer system modified with mixed oxide in this way can now be used to produce an exhaust gas sensor for oxygen, carbon monoxide, nitrogen oxides or hydrocarbons.

We claim:

1. A layer system for a gas sensor, comprising:
   (a) a substrate (10),
   (b) an electrode layer (11); and
   (c) at least one porous ceramic covering layer (12) comprising at least one mixed oxide of at least one light alkali metal oxide selected from the group consisting of lithium, sodium and potassium together with at least one thermally stable oxide of an element having a valence of at least three, selected from the group consisting of B, Al, Ga, In, Tl, Sc, Y, La, Ti, Zr, Hf, and elements from the Lanthanide Series.

2. The layer system according to claim 1, wherein the mixed oxide contains 0.2 to 99.8 mol % alkali metal oxide in proportion to 100 mol % of mixed oxide.

3. The layer system according to claim 1, wherein the mixed oxide contains 0.2 to 99.8 mol % of thermally stable oxides in relation to 100 mol % of mixed oxide.

4. The layer system according to claim 1, further comprising an additional covering layer (14) of a mixed oxide according to claim 1.

5. A process for producing a layer system according to claim 4, comprising the steps of:
   (a) depositing an electrode layer (11) on a substrate (10);
   (b) depositing a porous ceramic covering layer (12) having mixed oxides of at least one light alkali metal oxide of lithium, sodium or potassium in addition to at least one thermally stable oxide of an element having a valence of at least three, selected from the group consisting of B, Al, Ga, In, Tl, Sc, Y, La, Ti, Zr, Hf, and elements from the Lanthanide Series, onto the electrode layer of step a;
   (c) sintering the layer system of steps (a) and (b);
   (d) depositing, by plasma spraying, an additional porous ceramic covering layer (14) of mixed oxides according to claim 1; and
   (e) subsequently sintering the layer system of steps (a) (b) (c) and (d).

6. The layer system according to claim 4 wherein at least one porous, ceramic covering layer contains catalyst substances for the purpose of adjusting a control point of the sensor.

7. In a gas sensor, the improvement comprising a layer system for determining gases selected from the group consisting of oxygen, carbon monoxide, nitrogen oxides and hydrocarbons in exhaust gases from motor vehicles according to claim 4.

8. The layer system according to claim 1 wherein the porous, ceramic covering layer contains catalyst substances for the purpose of adjusting a control point of the sensor.

9. A process for producing a layer system according to claim 1, comprising the steps of:
   (a) depositing an electrode layer (11) on a substrate (10);
   (b) depositing a porous, ceramic covering layer (12) on the electrode layer forming a layer system;
   (c) sintering the layer system (10, 11, 12);
   (d) subsequently, impregnating the porous, ceramic covering layer (12) with a liquid containing at least one dissolved compound of an element, whose oxide is thermally stable; and
   (e) drying said layer system of steps (a), (b), (c) and (d).

10. A process according to claim 9, wherein the impregnating liquid is a solution of inorganic salt compounds.

11. A process according to claim 10, wherein the inorganic salt compounds are chlorides and nitrates.

12. A process according to claim 9, wherein the impregnating liquid contains organic metal compounds.

13. A process for producing a layer system according to claim 1, comprising the steps of:
   (a) depositing an electrode layer (11) on a substrate (10);
   (b) depositing, by plasma spraying, a porous ceramic covering layer (12) having mixed oxides of at least one light alkali metal oxide of lithium, sodium or potassium in addition to at least one thermally stable oxide of an element having a valence of at least three, selected from the group consisting of B, Al, Ga, In, Tl, Sc, Y, La, Ti, Zr, Hf, and elements from the Lanthanide Series, onto the electrode layer of step a; and
   (c) subsequently sintering the layer system of steps (a) and (b).

14. In a gas sensor, the improvement comprising a layer system for determining gases selected from the group consisting of oxygen, carbon monoxide, nitrogen oxides and hydrocarbons in exhaust gases from motor vehicles according to claim 1.

* * * * *